United States Patent
Bodner (10) Patent No.: US 11,344,714 B2
(45) Date of Patent: May 31, 2022

(54) INTRATHECAL CATHETER WITH FEATURES TO REDUCE DRUG DISPERSION

(71) Applicant: Medtronic, Inc., Minneapolis, MN (US)

(72) Inventor: Jeffrey Bodner, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 312 days.

(21) Appl. No.: 16/672,745

(22) Filed: Nov. 4, 2019

(65) Prior Publication Data
US 2021/0128900 A1  May 6, 2021

(51) Int. Cl.
A61M 39/02 (2006.01)
A61M 5/142 (2006.01)
A61M 25/00 (2006.01)

(52) U.S. Cl.
CPC .... *A61M 39/0247* (2013.01); *A61M 5/14276* (2013.01); *A61M 25/0021* (2013.01); *A61M 2039/0273* (2013.01); *A61M 2039/0276* (2013.01); *A61M 2039/0282* (2013.01)

(58) Field of Classification Search
CPC .... A61M 2025/006; A61M 2025/0073; A61M 2039/0009; A61M 2039/0273; A61M 2039/0276; A61M 2039/0282; A61M 25/0021; A61M 25/007; A61M 39/00; A61M 39/02; A61M 39/0247; A61M 5/14276
See application file for complete search history.

(56) References Cited

U.S. PATENT DOCUMENTS

| | | | |
|---|---|---|---|
| 4,502,488 A | 3/1985 | DeGironimo et al. |
| 4,730,623 A | 3/1988 | Lee |
| 4,731,051 A | 3/1988 | Fischell et al. |
| 4,834,709 A | 5/1989 | Banning et al. |
| 5,807,324 A | 9/1998 | Griffin, III |

(Continued)

FOREIGN PATENT DOCUMENTS

| | | |
|---|---|---|
| EP | 0226220 A2 | 6/1987 |
| EP | 1 345 640 B1 | 9/2003 |

(Continued)

OTHER PUBLICATIONS

Extended European Search Report for European Application No. 19179065.8, dated Aug. 9, 2019.

(Continued)

*Primary Examiner* — Brandy S Lee
(74) *Attorney, Agent, or Firm* — Patterson Thuente Pedersen, P.A.

(57) ABSTRACT

A medical device configured to restrict medicament dispersion within a cerebrospinal fluid flow of the patient. The medical device including an implantable catheter having a distal end configured to be positioned within a flow of the cerebrospinal fluid, a proximal end, a body defining a lumen extending lengthwise along the implantable catheter configured to enable a flow of medicament from the proximal end to an infusion port located in proximity to the distal end, and a contoured surface defined by an exterior of the body in proximity to the infusion port configured to inhibit dispersion of the medicament within the cerebrospinal fluid.

13 Claims, 7 Drawing Sheets

(56) References Cited

U.S. PATENT DOCUMENTS

| | | |
|---|---|---|
| 5,897,528 A | 4/1999 | Schultz |
| 6,013,051 A | 1/2000 | Nelson |
| 6,579,280 B1 | 6/2003 | Kovach et al. |
| 6,807,965 B1 | 10/2004 | Hickle |
| 7,072,802 B2 | 7/2006 | Hartlaub |
| 7,192,414 B2 | 3/2007 | Stultz |
| 7,438,701 B2 | 10/2008 | Theeuwes et al. |
| 7,593,770 B2 | 9/2009 | Lerner |
| 7,651,518 B2 | 1/2010 | Dobak, III et al. |
| 7,806,886 B2 | 10/2010 | Kanderian et al. |
| 8,486,023 B2 | 7/2013 | Pyles |
| 9,122,785 B2 | 9/2015 | Alme et al. |
| 9,655,528 B2 | 5/2017 | Zhu |
| 9,682,193 B2 | 6/2017 | Anand et al. |
| 9,770,180 B2 | 9/2017 | Radojicic |
| 2001/0044588 A1 | 11/2001 | Mault |
| 2006/0064009 A1 | 3/2006 | Webler et al. |
| 2006/0178617 A1 | 8/2006 | Adams et al. |
| 2007/0073250 A1 | 3/2007 | Schneiter |
| 2007/0137296 A1 | 6/2007 | Krivitski et al. |
| 2008/0146990 A1 | 6/2008 | Jenson et al. |
| 2010/0125246 A1 | 5/2010 | Kalpin |
| 2011/0238039 A1 | 9/2011 | Leonard et al. |
| 2011/0245766 A1 | 10/2011 | Leonard et al. |
| 2012/0197322 A1 | 8/2012 | Skelton |
| 2012/0245562 A1 | 9/2012 | Bihlmaier |
| 2013/0267928 A1* | 10/2013 | Imran ............ A61M 5/14276 604/500 |
| 2013/0296823 A1 | 11/2013 | Melker et al. |
| 2014/0228765 A1 | 8/2014 | Burke et al. |
| 2015/0297874 A1 | 10/2015 | East et al. |
| 2017/0203084 A1 | 7/2017 | Lad et al. |
| 2019/0160254 A1 | 5/2019 | Anand et al. |
| 2019/0388663 A1 | 12/2019 | Bodner et al. |
| 2020/0016368 A1 | 1/2020 | Bodner et al. |

FOREIGN PATENT DOCUMENTS

| | | |
|---|---|---|
| WO | WO2004100769 | 11/2004 |
| WO | WO2006002275 | 1/2006 |
| WO | WO2011140118 A1 | 11/2011 |
| WO | WO2017122199 | 7/2017 |
| WO | WO2018005169 | 1/2018 |
| WO | WO2018119179 | 6/2018 |

OTHER PUBLICATIONS

Sakka et al., "Anatomy and physiology of cerebrospinal fluid," European Annals of Otorhinolaryngology, Head and Neck diseases (2011) 128, 309-316. Available online Nov. 18, 2011.

U.S. Appl. No. 16/508,442, filed Jul. 11, 2019, Inventor(s): Bodner et al.

U.S. Appl. No. 16/572,763, filed Sep. 17, 2019, Inventor(s): Bodner.

International Search Report and Written Opinion for PCT/US2020/058462, dated Apr. 8, 2021, 13 pages.

International Search Report and Written Opinion for PCT/US2020/043252, dated Oct. 5, 2021, 12 pages.

International Search Report and Written Opinion for PCT/US2020/043249, dated Nov. 16, 2020, 10 pages.

Extended European Search Report for European Application No. 19185551.9, dated Dec. 18, 2019.

Office Action for European Application No. 19179065.8, dated Sep. 10, 2020, 6 pages.

K. Tangen, I. Nestorov, A. Verma, J. Sullivan, R.W. Holt and A.A. Linninger, "In Vivo Intrathecal Tracer Dispersion in Cynomolgus Monkey Validates Wide Biodistribution Along Neuraxis," in IEEE Transactions on Biomedical Engineering, vol. 6, pp. 1122-1132, Apr. 2020 (Year: 2019).

* cited by examiner

INTRATHECAL CATHETER WITH FEATURES TO REDUCE DRUG DISPERSION

FIELD

The present technology is generally related to implantable medical devices, and more particularly to a system and method utilizing an implantable catheter configured to minimize or delay medicament dispersion within the cerebrospinal fluid of a patient, or otherwise restrict the infused medicament to specific areas within the central nervous system.

BACKGROUND

Implantable medical devices, such as an implantable access port or medical pump, are useful in managing the delivery and dispensation of prescribed therapeutic agents, nutrients, drugs, medicaments such as antibiotics, blood clotting agents, analgesics and other fluid and/or fluid like substances (collectively "medicaments" or "infusates") to patients in volume- and time-controlled doses. Such implantable devices are particularly useful for treating diseases and disorders that require regular or chronic (i.e., long-term) pharmacological intervention, including tremor, spasticity, multiple sclerosis, Alzheimer's disease, Parkinson's disease, amyotrophic lateral sclerosis (ALS), Huntington's disease, cancer, epilepsy, chronic pain, urinary or fecal incontinence, sexual dysfunction, obesity, and gastroparesis, to name just a few. Depending upon their specific designs and intended uses, implantable devices are well adapted to administer infusates to specific areas within the central nervous system, including the subarachnoid, epidural, intrathecal, and intracranial spaces.

Administration of infusates directly into the cerebrospinal fluid of a patient has a number of important advantages over other forms of medicament administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood-brain barrier adequately if needed in the brain. In addition, infusion of substances from outside the body requires a transcutaneous catheter, which results in other risks such as infection or catheter dislodgment.

Typically, such implantable medical devices include an implantable catheter in fluid communication with an implantable access port or an implantable pump. Implantable access ports are typically placed cranially or over the ribs, and are connected to a catheter which is surgically placed in the intraventricular space of the brain or intraspinal area of the spinal cord. When it is desirable to administer a medicament, a needle is inserted through the patient's skin, through a septum of the port, which is in fluid connection with the catheter. The medicament is then injected into the port where it passes through the catheter and into the patient's cerebrospinal fluid.

Implantable pumps are typically implanted at a location within the body of a patient (typically a subcutaneous region in the lower abdomen), and are connected to a catheter configured to deliver medicament to a selected delivery site in the patient. Such implantable medical pumps typically include an expandable fluid reservoir, which is accessible for refill etc. through an access port. Medicament flows from the reservoir through the catheter and into the patient's cerebrospinal fluid according to programmed parameters.

The catheter is generally configured as a flexible tube with a lumen running the length of the catheter to a selected delivery site in the body, such as the subarachnoid space. Drug molecules exiting the catheter lumen flow into the subarachnoid space, and begin mixing with the cerebrospinal fluid. Frequently, the drug exits the catheter, and a natural pulsatile flow of the cerebrospinal fluid causes the infused drug to spread throughout the central nervous system. Although various attempts have been made to improve dispersion of the infused drug within the cerebrospinal fluid, little or no attempt has been made to reduce drug dispersion. For certain types of therapies, for example treatment of a spinal injury, it may be advantageous to minimize or delay drug dispersion within the cerebrospinal fluid, or otherwise to restrict the infused drug to a specific area within the central nervous system for localized treatment. The present disclosure addresses this concern.

SUMMARY

The techniques of this disclosure generally relate to implantable systems and methods configured to reduce medicament dispersion within a flow of cerebrospinal fluid of a patient through the use of an implantable catheter having a contoured exterior surface in proximity to an infusion port configured to inhibit dispersion of medicament within the cerebrospinal fluid. Accordingly, embodiments of the present disclosure optimize current therapy techniques by minimizing or delaying dispersion of infused medicament, or otherwise restricting the infused medicament, with the goal of improving patient outcomes and reducing side negative effects by localizing treatment to a specific area within the central nervous system. Although applications of the present disclosure can be used for the delivery of any type of medicament, it is believed that the present disclosure may be particularly useful in targeting specific proteins or viruses in the treatment of a particular disability, disorder or disease, as opposed to merely addressing undesirable symptoms.

One embodiment of the present disclosure provides a medical device configured to restrict medicament dispersion. The medical device can include an implantable catheter having a distal end configured to be positioned within a flow of cerebrospinal fluid of the patient, a proximal end, and a body defining a lumen extending lengthwise along the implantable catheter configured to enable a flow of medicament from the proximal end to an infusion port positioned in proximity to the distal end, the implantable catheter further including a contoured surface defined by an exterior of the body in proximity to the infusion port configured to inhibit dispersion of the medicament within the cerebrospinal fluid.

In one embodiment, the contoured surface is configured to increase a depth of a slower moving boundary layer of cerebrospinal fluid surrounding the body of the implantable catheter during medicament dispersion. In one embodiment, the contoured surface includes one or more circumferential ring extending radially outward from a longitudinal axis of the body of the implantable catheter. In one embodiment, the one or more circumferential ring includes at least one surface extending radially outward from the body of the implantable catheter positioned in proximity to the infusion port, and configured to shield the infusion port from a natural flow of cerebrospinal fluid. In one embodiment, the contoured surface includes at least a pair of circumferential rings, with a first circumferential ring positioned distally to the infusion port and a second circumferential ring position proximally to the infusion port, thereby defining a channel therebetween in which the infusion port is positioned. In one embodiment, the contoured surface includes one or more laterally extending portions configured to act as a barrier between infused medicament and a natural flow of cerebrospinal fluid. In one embodiment, the contoured surface includes a pair of opposed laterally extending portions. In one embodiment, the implantable catheter includes a plurality of infusion ports. In one embodiment, the plurality of infusion ports are aligned along a longitudinal axis of the body of the implantable catheter.

Another embodiment of the present disclosure provides a method of improving medicament dispersion, including: administering medicament into a flow of cerebrospinal fluid of a patient via an implantable catheter having a distal end configured to be positioned within the flow of cerebrospinal fluid, a proximal end, a body defining a lumen configured to enable a flow of medicament to an infusion port positioned in proximity to the distal end, and a contoured surface defined by an exterior of the body in proximity to the infusion port configured to inhibit dispersion of the medicament within the cerebrospinal fluid.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 1:
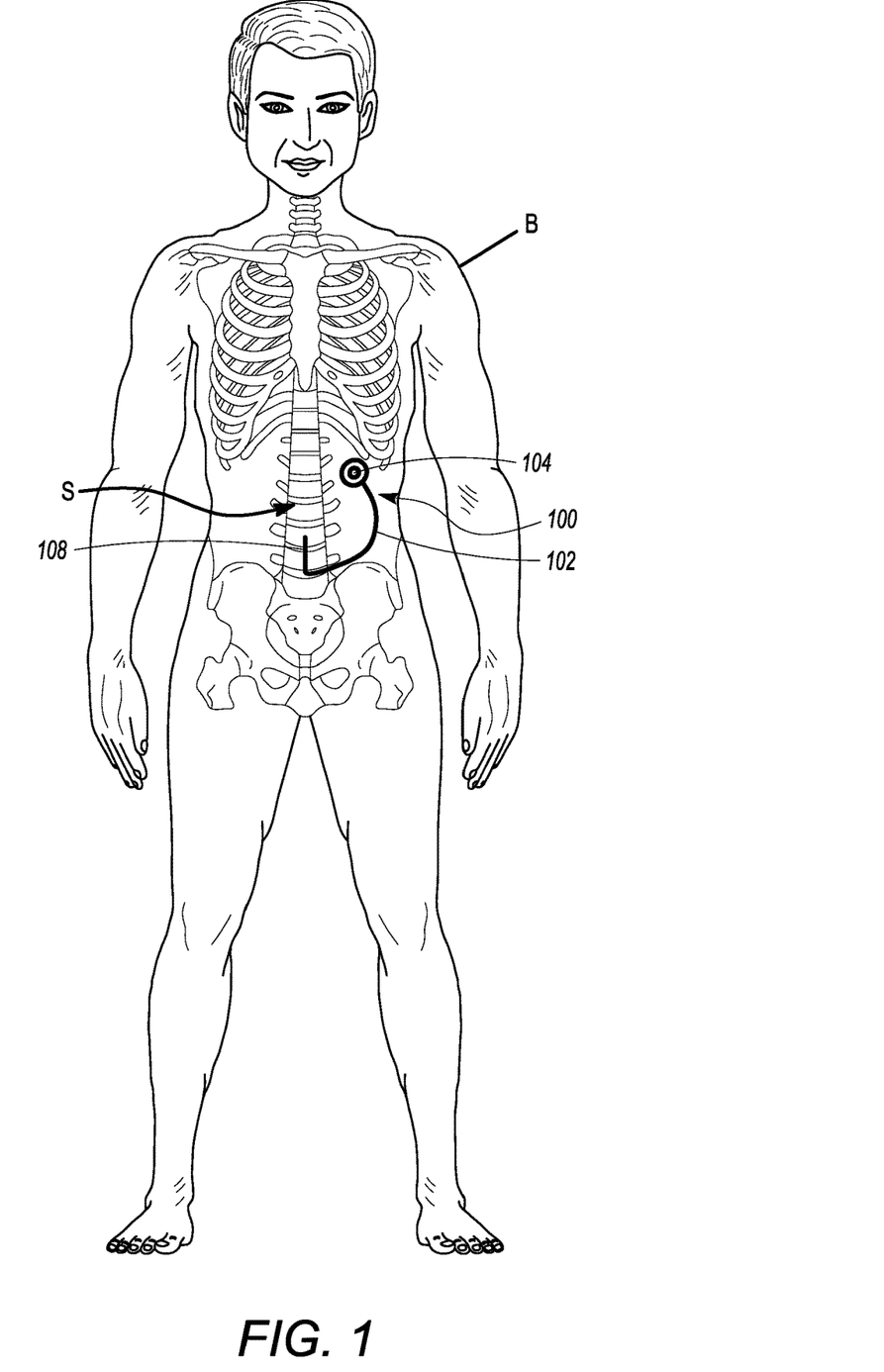
FIG. 1 depicts a medical device configured to improve medicament dispersion having a catheter inserted into an intrathecal space of a patient's spinal column, in accordance with an embodiment of the disclosure.

Referring to FIG. 1, a medical device 100 configured to improve medicament dispersion is depicted in accordance with an embodiment of the disclosure. The medical device 100 can include an implantable catheter 102, which can be in fluid communication with either an implantable port or pump 104. As depicted, the medical device 100 can be implanted within the body B of a patient. In some embodiments, a distal tip 108 of the implantable catheter 102 can optionally be surgically implanted in a patient's intraspinal space. The implantable port or pump 104 can be placed subcutaneously in proximity to the patient's ribs or in an interior torso cavity, and can be held in position by sutures or other retaining features.

Figure 2:
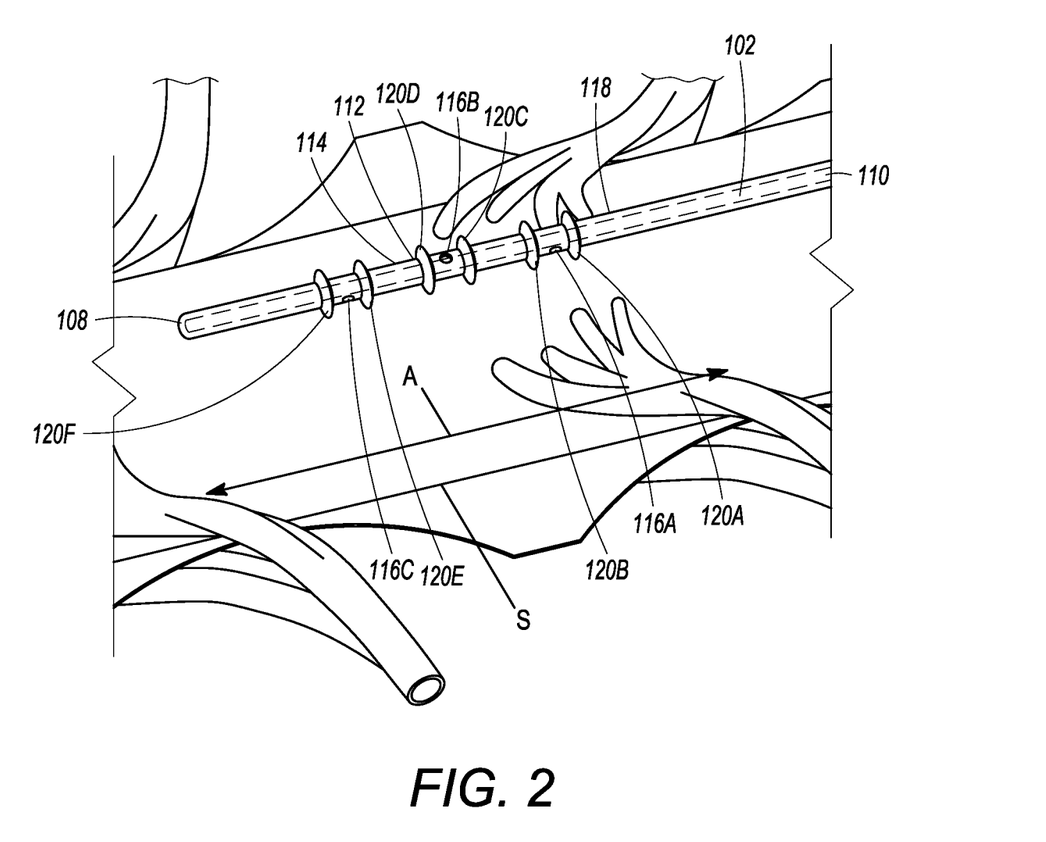
FIG. 2 is a perspective view depicting a catheter having a contoured surface configured to inhibit dispersion of medicament within cerebrospinal fluid of the patient, in accordance with an embodiment of the disclosure.

FIG. 2 depicts a catheter 102 positioned within a subarachnoid space of a patient, in accordance with an embodiment of the disclosure. In particular, the catheter 102 is inserted into the subarachnoid space to extend substantially parallel to a longitudinal axis A of the patient's spinal column, thereby enabling intrathecal delivery of medicament into the cerebrospinal fluid within the patient's spinal column. As depicted, the implantable catheter 102 can include a distal end 108, a proximal end 110, and a body 112 defining a lumen 114 extending lengthwise along the implantable catheter 102 and configured to enable a flow of medicament from the proximal end 110 to one or more infusion ports 116A-C positioned in proximity to the distal end 108. For example, in one embodiment, the implantable catheter 102 can include a plurality of infusion ports 116A-C aligned along a longitudinal axis of the body 112 of the implantable catheter 102. In one embodiment, the infusion ports 116A-C can be configured as throughbore ports, which can be rotated with respect to one another (e.g., unaligned with one another) along a longitudinal axis of the body 112 of the implantable catheter 102.

During infusion, medicament can flow from the proximal end 110 of the catheter 102, through the lumen 114, to exit the catheter body 112 through the one or more infusion ports 116A-C. Thereafter mixing of the medicament with the cerebrospinal fluid can commence. In some embodiments, it may be desirable to inhibit, restrict or delay dispersion of the medicament within the cerebrospinal fluid. That is, with some treatments, an improved therapeutic outcome may result if the medicament can be maintained in a localized area within a patient at a higher concentration for an extended period of time. For example, it may be desirable to maintain a higher concentration of infused proteins at the localized sight of a spinal cord injury of a patient for as long as possible after infusion. In other cases, localization of the medicament may result in improved therapeutic outcomes by enabling infused medicament to be absorbed by the spinal cord in a more localized area and reduce any negative side effects from a more rapid dispersion of the medicament within the cerebrospinal fluid.

With continued reference to FIG. 2, in order to inhibit the dispersion of medicament within the cerebrospinal fluid, in some embodiments, an exterior 118 of the body 112 can define one or more contoured surfaces 120A-F in proximity to the infusion ports 116A-C. The one or more contoured surfaces 120A-F can be configured to increase the depth or thickness of a slower moving boundary layer of cerebrospinal fluid immediately surrounding the body 112 of the catheter 102 during medicament dispersion, thereby slowing a mixing of the medicament with the cerebrospinal fluid so as to maintain a higher concentration of medicament at a localized area within the cerebrospinal fluid for a longer period of time.

In one embodiment, the contoured surfaces 120 can generally be configured as circumferential saucers or disk-shaped rings extending radially outward from a longitudinal axis of the body 112 of the implantable catheter 102. In some embodiments, the contoured surfaces 120 can be positioned in proximity to an infusion port 116, so as to shield the infusion port 116 from a natural flow of cerebrospinal fluid. In some embodiments, a pair of contoured surfaces 120A/B can be positioned on opposing sides of an infusion port 116A so as to define a channel in which the infusion port 116A is positioned.

Figure 3A:
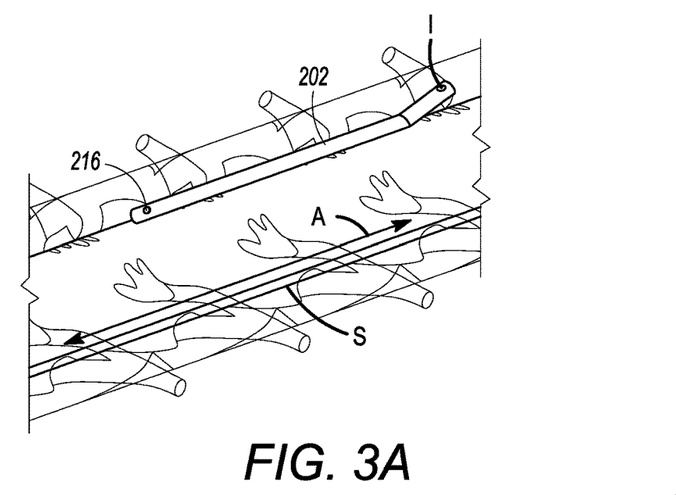
FIG. 3A is a perspective view depicting a catheter inserted into a subarachnoid space of a patient, in accordance with the prior art.
Figure 3B:
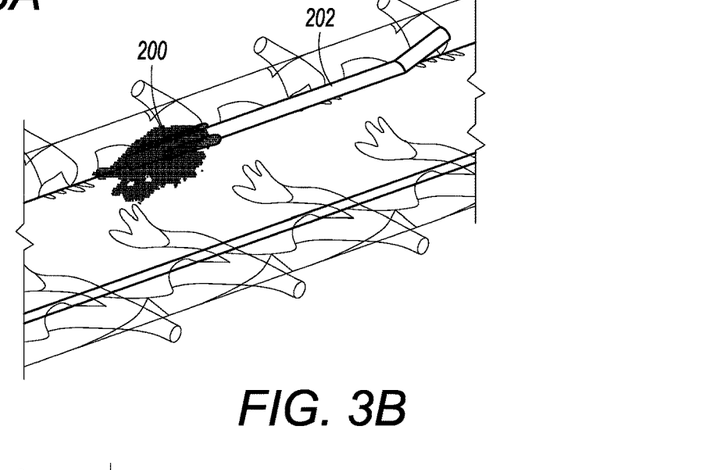
FIG. 3B depicts the dispersion of medicament within the cerebrospinal fluid of a patient after approximately 7.5 seconds of initiating infusion from the catheter of FIG. 3A.
Figure 3C:
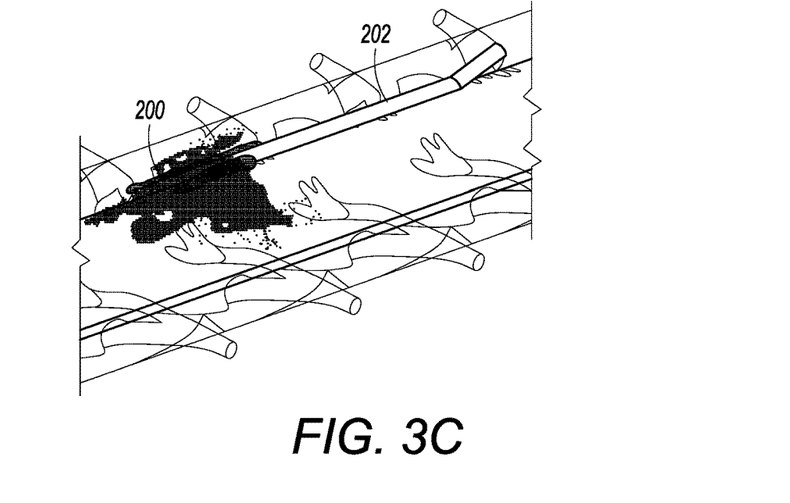
FIG. 3C depicts the dispersion of medicament within the cerebrospinal fluid of a patient after approximately 15 seconds of initiating infusion from the catheter of FIG. 3A.

For comparative purposes, FIGS. 3A-C depict the infusion of medicament into the subarachnoid space of the patient through an implantable catheter of the prior art. FIG. 3A depicts the catheter 202 having entered the subarachnoid space at an insertion site I, and extending substantially parallel to a longitudinal axis A of the patient's spinal column S, thereby enabling intrathecal delivery of medicament through an infusion port 216 of the catheter 202. FIGS. 3B and 3C depict the catheter 202 as the medicament 200 exits the infusion port 216 and flows into the subarachnoid space. Specifically, FIG. 3B depicts the dispersion of medicament 200 after approximately 7.5 seconds of initiating infusion, and FIG. 3C depicts the dispersion of medicament 200 after approximately 15 seconds of initiating infusion.

As the medicament 200 exits the infusion port 216 and flows into the subarachnoid space, the medicament 200 begins mixing with the cerebrospinal fluid. The medicament 200, which may be expelled from the infusion port 216 (e.g., at a flow rate of 1 mL per hour) enters the slow-moving boundary layer of cerebral spinal fluid immediately surrounding the catheter 202. Thereafter, a natural pulsatile flow of the cerebrospinal fluid causes the medicament 200 to drift away from the boundary layer into faster moving cerebrospinal fluid (as depicted in FIGS. 3B and 3C).

Figure 4A:
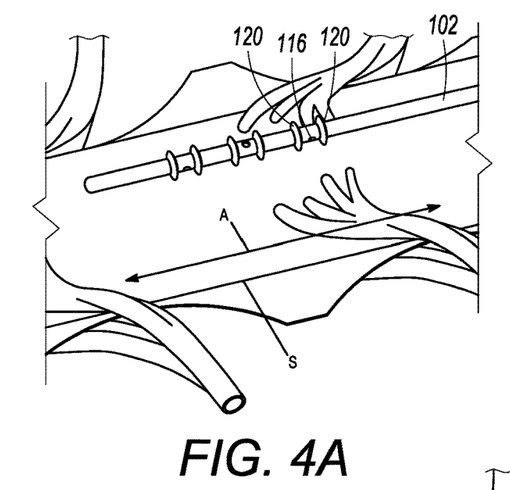
FIG. 4A is a perspective view depicting a catheter having a contoured surface configured to inhibit dispersion of infused medicament into a subarachnoid space of a patient, according to a first embodiment of the disclosure.
Figure 4B:
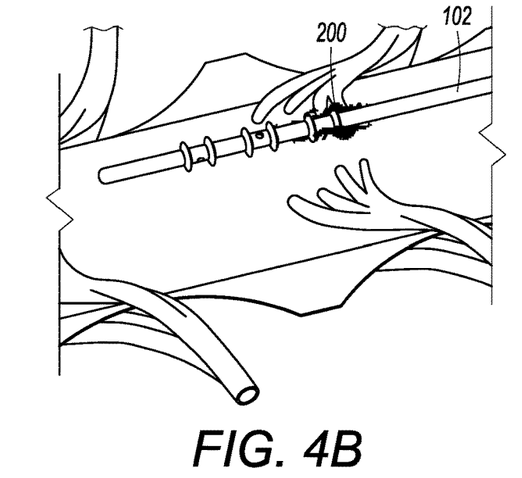
FIG. 4B depicts the dispersion of medicament within the cerebrospinal fluid of a patient after approximately 7.5 seconds of initiating infusion from the catheter of FIG. 4A.
Figure 4C:
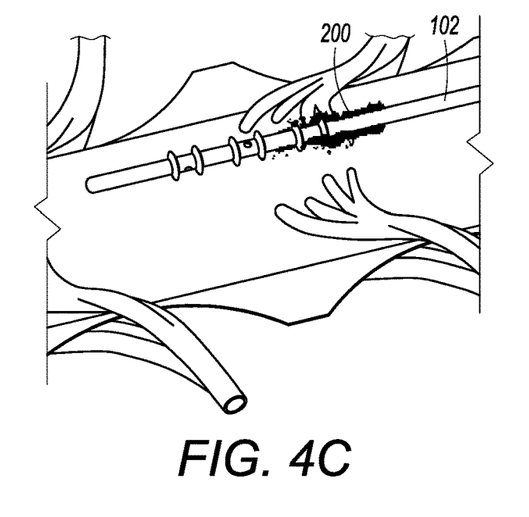
FIG. 4C depicts the dispersion of medicament within the cerebrospinal fluid of a patient after approximately 15 seconds of initiating infusion from the catheter of FIG. 4A.

FIGS. 4A-C, 5A-C and 7A-C represent predictions of respective volumes of dispersed clouds of medicament 200 through embodiments of implantable catheters 102, 102', and 102" of the present disclosure having contoured surfaces 120 configured to inhibit the dispersion of the medicament 200 within the cerebrospinal fluid. In particular, FIG. 4A depicts the catheter 102 of FIG. 2 positioned within the subarachnoid space, so as to extend substantially parallel to a longitudinal axis A of the patient was spinal column, thereby enabling intrathecal delivery of medicament through the infusion port 116. FIGS. 4B and 4C depict the catheter 102 as the medicament 200 exits the infusion port 116 and flows into the subarachnoid space. Specifically, FIG. 4B depicts the dispersion of medicament 200 after approximately 7.5 seconds of initiating infusion, and FIG. 4C depicts the dispersion of medicament 200 after approximately 15 seconds of initiating infusion.

Figure 5A:
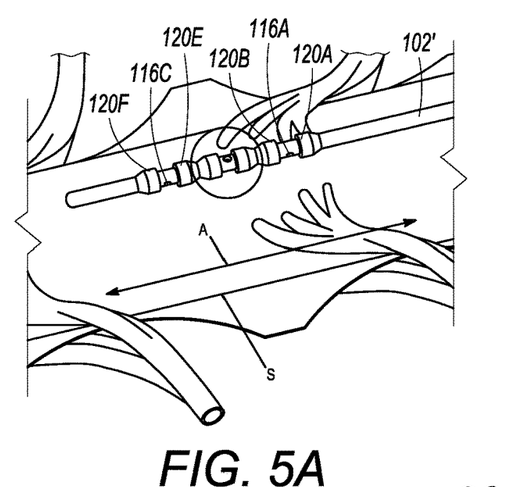
FIG. 5A is a perspective view depicting a catheter having a contoured surface configured to inhibit dispersion of infused medicament inserted into a subarachnoid space of a patient, according to a second embodiment of the disclosure.
Figure 5B:
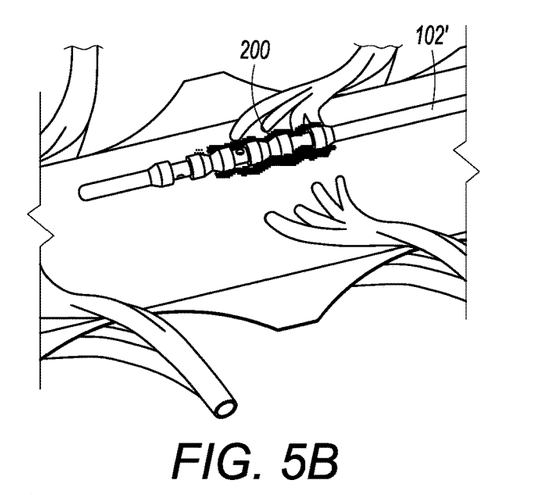
FIG. 5B depicts the dispersion of medicament within the cerebrospinal fluid of a patient after approximately 7.5 seconds of initiating infusion from the catheter of FIG. 5A.
Figure 5C:
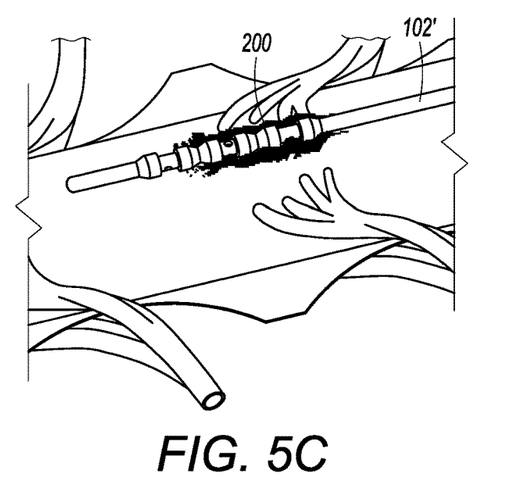
FIG. 5C depicts the dispersion of medicament within the cerebrospinal fluid of a patient after approximately 15 seconds of initiating infusion from the catheter of FIG. 5A.
Figure 6:
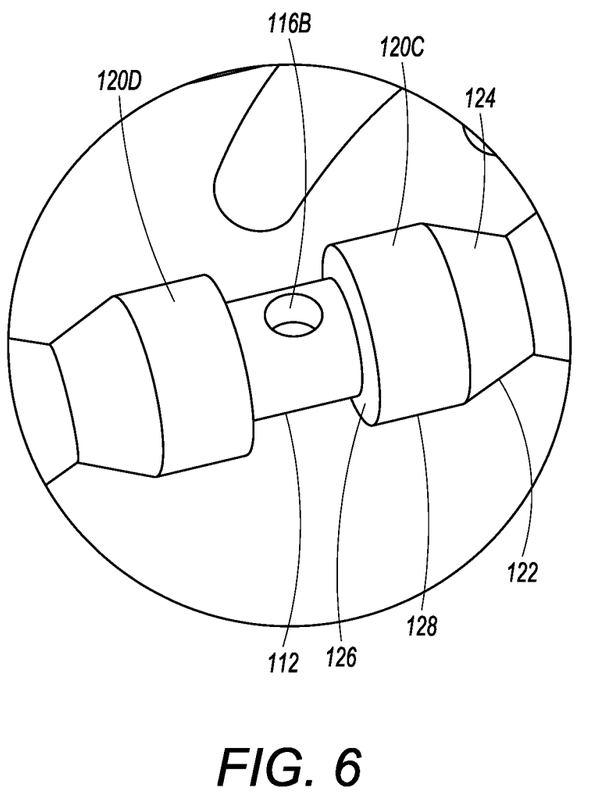
FIG. 6 is a close-up view of the contoured surface of the catheter depicted in FIG. 5A.

FIGS. 5A-C depict an alternative embodiment of the implantable catheter 102' in which the contoured surfaces 120A-F are generally configured as circumferential projections extending radially outward from a longitudinal axis of the body 112 at the implantable catheter 102'. For example, as depicted in FIG. 6 (which depicts a partial, detailed view of the catheter 102' of FIG. 5A), each contoured surface 120 can include a frustoconical portion 122 having a first radial (often gradual) taper 124 generally extending away from the infusion port 116, and a second radial (often steeper) taper 126 extending towards or positioned adjacent to the infusion port 116. In one embodiment, the first radial taper 124 can have a taper angle of between about 30° and about 60°, and the second radial taper 126 can have a taper angle of between about 60° and about 90°; although other taper angles are also contemplated. In some embodiments, the contoured surface 120 can further include a landing 128 in the shape of a cylinder having a substantially uniform outer diameter.

With continued reference to FIG. 6, in some embodiments, a pair of contoured surfaces 120C/D can be positioned on opposing sides of an infusion port 116B, so as to define a channel in which the infusion port 116B is positioned. Accordingly, the portion of the body 112 of the catheter 102' positioned between the pair of contoured surfaces 120C/D can have a substantially uniform outer diameter that is generally smaller than the outer diameter of the adjacent contoured surfaces 120C/D, such that the defined channel can generally serve as a barrier to naturally contain medicament as it is dispensed from the infusion port 116B. In other embodiments, a single contoured surface 120 can be positioned on either side of the infusion port 116.

FIGS. 5B and 5C depict the catheter 102' as the medicament 200 exits the infusion ports 116A-C and flow into the subarachnoid space. Specifically, FIG. 5B depicts the dispersion of medicament 200 after approximately 7.5 seconds of initiating infusion, and FIG. 5C depicts the dispersion of medicament 200 after approximately 15 seconds of initiating infusion.

Figure 7A:
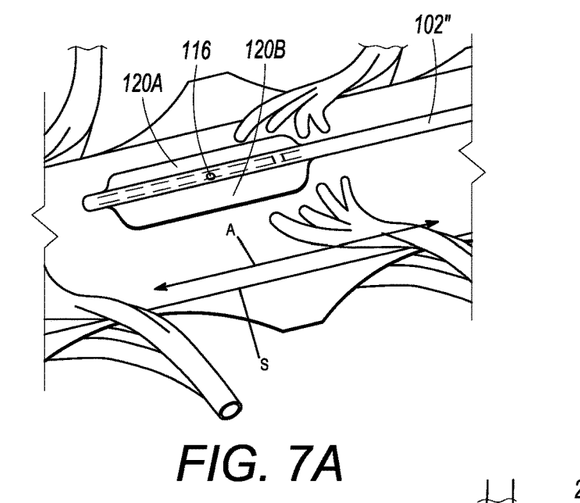
FIG. 7A is a perspective view depicting a catheter having a contoured surface configured to inhibit dispersion of infused medicament inserted into a subarachnoid space of a patient, according to a third embodiment of the disclosure.
Figure 7B:
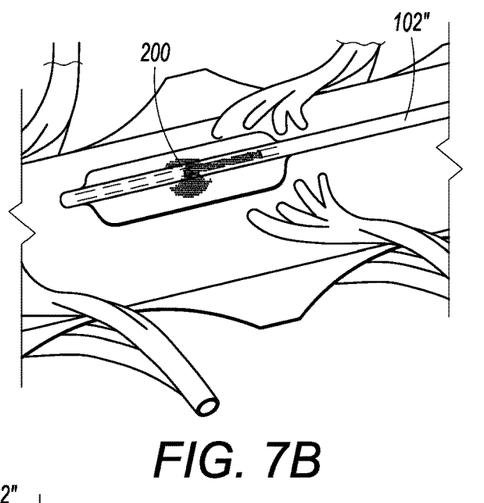
FIG. 7B depicts the dispersion of medicament within the cerebrospinal fluid of a patient after approximately 7.5 seconds of initiating infusion from the catheter of FIG. 7A.
Figure 7C:
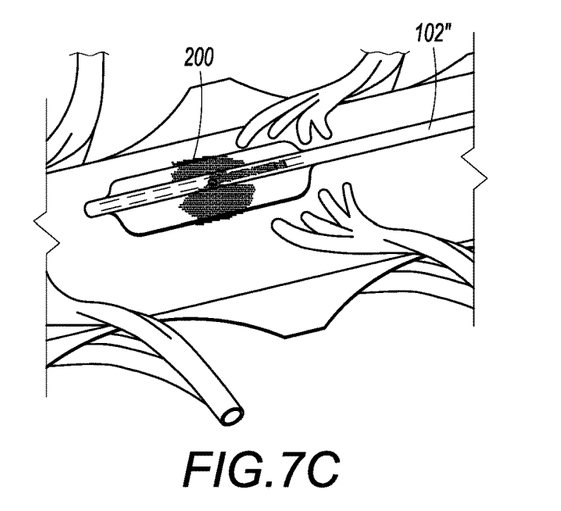
FIG. 7C depicts the dispersion of medicament within the cerebrospinal fluid of a patient after approximately 15 seconds of initiating infusion from the catheter of FIG. 7A.

FIGS. 7A-C depict yet another embodiment of the implantable catheter 102" in which the contoured surfaces 120A-B are configured as wings or flaps that extend laterally outward from the implantable catheter 102", thereby enabling medicament dispensed from the infusion port 116 to generally be trapped between the contoured surfaces 120A-B and a localized interior surface of an intrathecal space of a patient. For example, in one embodiment, the contoured surfaces 120A-B can extend laterally outward on opposing sides of the body 112 of the catheter 102″, so as to generally form a planar surface. In some embodiments, the contoured surfaces 120A-B can be constructed of a resilient material, thereby enabling the contoured surfaces 120A-B to be wrapped around the body 112 of the catheter 102″, and optionally held in position by a sheath (not depicted) for the purpose of minimizing and insertion profile of the catheter 102″. After insertion, a natural resiliency of the contoured surfaces 120A-B can cause the contoured surfaces 120A-B to extend to a substantially planar configuration, as depicted in FIGS. 7A-C.

FIGS. 7B and 7C depict the catheter 102″ as the medicament 200 exits the infusion ports 116A-C and flow into the subarachnoid space. Specifically, FIG. 7B depicts the dispersion of medicament 200 after approximately 7.5 seconds of initiating infusion, and FIG. 7C depicts the dispersion of medicament 200 after approximately 15 seconds of initiating infusion.

FIGS. 3A-C, 4A-C, 5A-C, and 7A-C represent predictions of respective volumes of dispersed clouds of medicament 200 in an idealized intrathecal space geometry with cerebrospinal fluid that oscillates according to a sine function with a 1 Hz frequency and 3 mL/s amplitude. With a nominal catheter 102 (such as that depicted in FIGS. 3A-C), at a time of 30 seconds after the start of a bolus infusion at 1 mL/hr, the infused medicament can occupy a volume of between about 25 mm$^3$ and about 500 mm$^3$. By contrast, for embodiments of the present disclosure, where the catheter 102, 102′, or 102″ includes one or more contoured surfaces 120 configured to inhibit dispersion of the medicament within the cerebrospinal fluid (such as that depicted in FIGS. 4A-C, 5A-C and 7A-C), with all other model parameters kept constant, the infused medicament 200 can occupy a volume of between about 12.5 mm$^3$ and about 25 mm$^3$. Thus, it can be seen that the contoured surfaces 120, as described above, can have the effect of decreasing the volume of dispersed medicament 200 by between approximately about 97% and about 50% with respect to that of a catheter without a contoured surface.

The dispersion of medicament 200 delivered via catheter 102 into the subarachnoid space (and other areas within the human body) can be simulated using fluid dynamics modeling methods such as finite volume, finite element, or finite difference techniques for finding approximate solutions to systems of partial differential equations. In the case of intrathecal delivery, the system of partial differential equations that model conservation of mass and momentum, also known as Navier-Strokes equations, can simulate cerebrospinal fluid flow. To be more precise, the equations for laminar, oscillating flow of an incompressible fluid with properties similar to water at body temperature can be used to simulate medicament 200 delivery scenarios. Medicament 200 dispersion can further be modeled using various techniques including the Eulerian passive scaler approach or the Lagrangian particle approach.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A medical device configured to restrict medicament dispersion, the medical device comprising:
   an implantable catheter having a distal end configured to be positioned within a flow of cerebrospinal fluid of a patient, a proximal end, and a body defining a lumen extending lengthwise along the implantable catheter configured to enable a flow of medicament from the proximal end to an infusion port positioned in proximity to the distal end, wherein an exterior of the body defines a first radially extending contoured surface and a second radially extending contoured surface are positioned on opposing sides of the infusion port so as to define a channel in which the infusion port is positioned configured to inhibit dispersion of the medicament within the cerebrospinal fluid.

2. The medical device of claim 1, wherein the contoured surface is configured to increase a depth of a slower moving boundary layer of cerebrospinal fluid surrounding the body of the implantable catheter during medicament dispersion.

3. The medical device of claim 1, wherein the contoured surface includes one or more circumferential ring extending radially outward from a longitudinal axis of the body of the implantable catheter.

4. The medical device of claim 3, wherein the one or more circumferential ring includes at least one surface extending radially outward from the body of the implantable catheter positioned in proximity to the infusion port, and configured to shield the infusion port from a natural flow of cerebrospinal fluid.

5. The medical device of claim 1, wherein the contoured surface includes at least a pair of circumferential rings, with a first circumferential ring positioned distally to the infusion port and a second circumferential ring positioned proximately to the infusion port, thereby defining a channel therebetween in which the infusion port is positioned.

6. The medical device of claim 1, wherein the contoured surface includes one or more laterally extending portions configured to act as a barrier between infused medicament and a natural flow of cerebral spinal fluid.

7. The medical device of claim 6, wherein the contoured surface includes a pair of opposed laterally extending portions.

8. The medical device of claim 1, wherein the implantable catheter includes a plurality of infusion ports.

9. The medical device of claim 8, wherein the plurality of infusion ports are aligned along a longitudinal axis of the body of the implantable catheter.

10. The medical device of claim 1, wherein each of the first and second radially extending contoured surfaces include a frustoconical portion having a first radial taper generally extending away from the infusion port, and a second radial taper generally extending towards the infusion port, wherein the second radial taper has a steeper taper angle than the first radial taper.

11. The medical device of claim 10, wherein the first radially extending contoured surface has a taper angle of between about 30° and about 60°, and wherein the second radially extending contoured surface has a taper angle of between about 60° and about 90°.

12. The medical device of claim 1, wherein each of the first and second radially extending contoured surfaces define a landing in the shape of a cylinder having a substantially uniform outer diameter.

13. A method of restricting medicament dispersion comprising:
administering medicament into a flow of cerebrospinal fluid of a patient via an implantable catheter having a distal end configured to be positioned within the flow of cerebrospinal fluid, a proximal end, a body defining a lumen configured to enable a flow of medicament to an infusion port positioned in proximity to the distal end, wherein an exterior of the body defines a first radially extending contoured surface and a second radially extending contoured surface are positioned on opposing sides of the infusion port so as to define a channel in which the infusion port is positioned configured to inhibit dispersion of the medicament within the cerebrospinal fluid.

* * * * *